United States Patent
Liu et al.

(10) Patent No.: US 9,180,430 B2
(45) Date of Patent: Nov. 10, 2015

(54) CATALYTIC COMPOSITION FOR PRODUCTION OF OLEFINS WITH DECREASED OXYGENATE BYPRODUCTS

(75) Inventors: Yu Liu, Lake Jackson, TX (US);
Andrzej M. Malek, Midland, MI (US);
Duncan Coffey, Lake Jackson, TX (US);
Eric E. Stangland, Midland, MI (US);
Albert E. Schweizer, Port St. Lucie, FL (US)

(73) Assignee: Dow Global Technologies LLC, Midland, MI (US)

( * ) Notice: Subject to any disclaimer, the term of this patent is extended or adjusted under 35 U.S.C. 154(b) by 45 days.

(21) Appl. No.: 13/634,619

(22) PCT Filed: Feb. 25, 2011

(86) PCT No.: PCT/US2011/000359
§ 371 (c)(1),
(2), (4) Date: Sep. 13, 2012

(87) PCT Pub. No.: WO2011/115656
PCT Pub. Date: Sep. 22, 2011

(65) Prior Publication Data
US 2013/0012749 A1    Jan. 10, 2013

Related U.S. Application Data

(60) Provisional application No. 61/340,356, filed on Mar. 16, 2010.

(51) Int. Cl.
| | | |
|---|---|---|
| C07C 1/22 | (2006.01) | |
| C07C 1/24 | (2006.01) | |
| C07C 1/00 | (2006.01) | |
| B01J 21/04 | (2006.01) | |
| B01J 21/12 | (2006.01) | |
| B01J 23/10 | (2006.01) | |
| B01J 37/00 | (2006.01) | |
| B01J 37/04 | (2006.01) | |
| C10G 3/00 | (2006.01) | |

(52) U.S. Cl.
CPC *B01J 21/04* (2013.01); *B01J 21/12* (2013.01); *B01J 23/10* (2013.01); *B01J 37/0036* (2013.01); *B01J 37/04* (2013.01); *C07C 1/24* (2013.01); *C10G 3/44* (2013.01); *C10G 3/49* (2013.01); *C10G 3/54* (2013.01); *C07C 2523/10* (2013.01); *C10G 2400/20* (2013.01); *C10G 2400/22* (2013.01)

(58) Field of Classification Search
CPC ..................... C07C 1/00; C07C 1/22
USPC ......................... 585/640, 639, 638
See application file for complete search history.

(56) References Cited

U.S. PATENT DOCUMENTS

| | | | |
|---|---|---|---|
| 3,836,603 A | 9/1974 | Connor et al. | |
| 4,234,752 A | 11/1980 | Wu et al. | |
| 4,615,863 A | 10/1986 | Inoue et al. | |
| 7,205,447 B2 * | 4/2007 | Levin et al. | 585/638 |
| 7,528,201 B2 | 5/2009 | Mertens et al. | |
| 2001/0038810 A1 | 11/2001 | Wallin et al. | |
| 2006/0025646 A1 | 2/2006 | Fung et al. | |
| 2007/0043250 A1 | 2/2007 | Xu et al. | |
| 2008/0058572 A1 | 3/2008 | Fernandez et al. | |
| 2009/0163687 A1 * | 6/2009 | Kaizik et al. | 526/348.6 |
| 2009/0180942 A1 | 7/2009 | Caudle | |
| 2010/0056816 A1 | 3/2010 | Wallin et al. | |

FOREIGN PATENT DOCUMENTS

| | | |
|---|---|---|
| CN | 101168124 | 4/2008 |
| CN | 101176850 | 5/2008 |
| EP | 0105591 A1 * | 8/1983 |
| EP | 0219609 | 4/1987 |
| JP | 2004290974 | 10/2004 |
| WO | 01/44145 | 6/2001 |
| WO | WO 2007134415 A2 * | 11/2007 |
| WO | 2011/002699 | 1/2011 |

OTHER PUBLICATIONS

International Search Report and Written Opinion from related PCT application PCT/US2011/000359 dated Apr. 19, 2011, 17 pages.
International Preliminary Report on Patentability from related PCT application PCT/US2011/000359 dated Jun. 14, 2012, 24 pages.
Inoue, et al. "Synthesis of LEV zeolite by interzeolite conversion method and its catalytic performance in ethanol to olefins reaction", Microporous and Mesoporous Materials, (2009), No. 122, 149-154.
Iwamoto, "Highly selective formation of lower olefins from bioethanol on nickel ion-loaded mesopourus silica catalysts", Abstracts of Papers, 235th ACS National Meeting, New Orleans, LA, US, Apr. 6-10, 2008, 1 page.
Iwamoto "One Step Formation of Propene from Ethene or Ethanol through Metathesis on Nickel Ion-loaded Silica", Molecules No. 16, 2011, 7844-7863.
Materials Letters; M.M. Doheim, et al., :"Catalytic conversion of ethanol and isopropanol over Mn2O3/Al2O3 system doped with Na2O", (8 pgs).

* cited by examiner

*Primary Examiner* — In Suk Bullock
*Assistant Examiner* — Youngsul Jeong
(74) *Attorney, Agent, or Firm* — Brooks, Cameron & Huebsch, PLLC

(57) ABSTRACT

Catalytic composition for production of olefins and methods of using same to decrease production of oxygenate byproducts. The catalytic composition includes an admixture of an alumina dehydration catalyst and at least one additional metal oxide.

8 Claims, No Drawings

CATALYTIC COMPOSITION FOR PRODUCTION OF OLEFINS WITH DECREASED OXYGENATE BYPRODUCTS

This application is a National Stage application under 35 U.S.C. 371 of PCT/US2011/000359, filed on Feb. 25, 2011 and published as WO2011/115656 A1 on Sep. 22, 2011, which claims the benefit of U.S. Provisional Application Ser. No. 61/340,356 filed Mar. 16, 2010, the entire contents of which are incorporated herein by reference in its entirety.

The present disclosure relates to a number of catalytic compositions for production of olefins, and in particular for improving production of olefins by alkanol dehydration by decreasing production of oxygenate byproducts.

Dehydration of alkanols that is intended to produce olefins often produces oxygenate byproducts. Alkanols are aliphatic alcohols, such as methanol, ethanol, propanol, butanol, or other alcohols with more carbon atoms in the aliphatic chain. The olefins produced from the alkanols have a carbon-carbon double bond in the aliphatic carbon chain. The oxygenate byproducts have at least one oxygen atom forming part of their molecular structure and include aldehydes, ketones, esters, ethers, other alcohols, carboxylic acids, etc. The oxygenate byproducts are undesired contaminants in an olefin product because, among other reasons, the oxygenate byproducts are reactive molecules that interfere with intended downstream reactions using the olefin product, e.g., polymerization of ethylene into polyethylene.

Units that function to remove the oxygenate byproducts, e.g., a distillation column for removal of aldehydes, can be placed downstream from a reactor in which the dehydration occurs. However, such units are expensive and/or complicate a process for producing the olefins. For instance, these units require capital input for purchase and installation, labor costs for operation and upkeep, and energy costs for operation. Hence, a catalytic composition that decreases production of oxygenate byproducts in situ while catalyzing alkanol dehydration is desirable relative to other catalysts and chemical reactions used to convert alkanols to olefins that produce more elevated amounts of oxygenate byproducts.

EXAMPLES (EXS)/COMPARATIVES (COMPS)

The following table shows the product results obtained with either the alumina dehydration catalyst gamma-alumina used by itself, as denoted by Comp 1, or the gamma-alumina in an admixture with an additional metal oxide, which is 25% by weight yttrium oxide, as denoted by Ex 1. These results are contrasted with product results obtained with either an amorphous aluminosilicate used by itself, as denoted by Comp 2, or the amorphous aluminosilicate in combination with 25% by weight yttrium oxide, as denoted by Comp 3.

|  |  | Exs/Comps | | | |
|---|---|---|---|---|---|
|  |  | Comp 1 | Ex 1 | Comp 2 | Comp 3 |
| Catalyst | | Alumina | Alumina + 25% $Y_2O_3$ | Aluminosilicate | Aluminosilicate + 25% $Y_2O_3$ |
| Temp (° C.) | | 400 | 400 | 400 | 400 |
| Product Concentration (mol %) | Carbon Dioxide | 0.09 | 3.45 | 0.00 | 3.61 |
| | Acetaldehyde | 1.09 | 0.00 | 0.27 | 0.23 |
| | Acetone | 0.16 | 0.51 | 0.01 | 0.46 |
| | Ethylene | 93.33 | 91.13 | 99.46 | 89.06 |
| | Ethane | 0.48 | 0.46 | 0.14 | 0.44 |
| | Propylene | 0.58 | 2.65 | 0.05 | 3.20 |
| | Propane | 0.00 | 0.00 | 0.00 | 0.00 |
| | Butene | 4.27 | 1.80 | 0.07 | 3.00 |
| | Butane | 0.00 | 0.00 | 0.00 | 0.00 |
| Total Product | | 100 | 100 | 100 | 100 |
| Total Oxygenates | | 1.25 | 0.51 | 0.28 | 0.69 |

Comp 1

Use a continuous flow fixed bed reactor system at ambient air pressure. Obtain the gamma-alumina dehydration catalyst in powdered form from Alfa Aesar. Crush the gamma-alumina and sieve through a 297-841 micrometer (μm) mesh. Position the crushed and sieved gamma-alumina in a single reaction zone of a stainless steel tube between 297-841 μm quartz chips in the reactor. Prior to the reaction, heat the gamma-alumina to 500 degrees Celsius (° C.) for 2 hours in argon gas to remove moisture. Lower the temperature to 400° C., which is the controlled reaction temperature. Feed ethanol to the single reaction zone using a pump with a fixed flow rate of 0.003 grams per minute (g/min). Dilute the ethanol with argon at 20 milliliters per minute (ml/min).

Expose the ethanol to the gamma-alumina to dehydrate the ethanol to produce desired olefin products and undesired byproducts, e.g., the oxygenate byproducts. Each of the desired products and undesired byproducts indicated in the table is shown with a molar percentage (mol %) of the total concentration of reaction product produced by exposure to the catalytic composition. In each Ex and Comp column, a cumulative total concentration of reaction product, as denoted by Total Product, is 100 mol %. The mol % values presented in the table represent an average data point value for 48 individual measurements by gas chromatography of samples taken over at least a 24 hour run of the continuous flow fixed bed reactor system.

A total concentration of oxygenate byproducts, as denoted by Total Oxygenates, is provided at the bottom of the table. In the present disclosure, total oxygenates include an additive concentration of light aldehyde and ketone byproducts. The light aldehyde and ketone byproducts formed by dehydration of ethanol using gamma-alumina or aluminosilicate, with or without yttrium oxide, are largely acetaldehyde and/or acetone, respectively. As such, total oxygenates is an additive concentration of acetaldehyde and/or acetone byproducts.

For Comp 1, the undesired acetaldehyde byproduct is 1.09 mol %, the undesired acetone byproduct is 0.16 mol %, and the total oxygenates is 1.25 mol %. The desired ethylene product is 93.33 mol %. Propylene is another desired product of a dehydration reaction using ethanol as the substrate. The desired propylene product is 0.58 mol %.

Ex 1

Replicate Comp 1 but form an admixture of 25% by weight of yttrium oxide ($Y_2O_3$) by physically mixing the yttrium oxide with the gamma-alumina. Yttrium oxide is prepared in-house by The Dow Chemical Company. Crush an admixture of 25% by weight of yttrium oxide and 75% by weight of gamma-alumina, both in powder form, and sieve through a 297-841 micrometer (μm) mesh.

For Ex 1, the undesired acetaldehyde byproduct is undetectable, i.e., is essentially zero mol %, the undesired acetone byproduct is 0.51 mol %, and the total oxygenates is also 0.51 mol %. The desired ethylene product is 91.13 mol % and the desired propylene product is 2.65 mol %.

Comp 2

Replicate Comp 1 but form a dehydration catalyst from amorphous aluminosilicate having a silicon (Si) to aluminum (Al) ratio (Si/Al) of 3.3 crushed and loaded through a 297-841 µm mesh. Obtain the amorphous aluminosilicate in powdered form from Sigma-Aldrich.

For Comp 2, the undesired acetaldehyde byproduct is 0.27 mol %, the undesired acetone byproduct is 0.01 mol %, and the total oxygenates is 0.28 mol %. The desired ethylene product is 99.46 mol % and the desired propylene product is 0.05 mol %.

Comp 3

Replicate Comp 2 but form an admixture of 25% by weight of yttrium oxide by physically mixing the yttrium oxide with the amorphous aluminosilicate. Crush an admixture of 25% by weight of yttrium oxide and 75% by weight of amorphous aluminosilicate, both in powder form, and sieve through a 297-841 micrometer (µm) mesh.

For Comp 3, the undesired acetaldehyde byproduct is 0.23 mol %, the undesired acetone byproduct is 0.46 mol %, and the total oxygenates is 0.69 mol %. The desired ethylene product is 89.06 mol % and the desired propylene product is 3.20 mol %.

The results in the table show that forming a catalytic composition including an admixture of gamma-alumina with yttrium oxide and exposing ethanol to the catalytic composition produces a mixture of desired products, e.g., ethylene and propylene, and undesired byproducts, including carbon dioxide ($CO_2$), in which the acetaldehyde mol % is essentially zero. Hence, addition of yttrium oxide to the gamma-alumina forms a catalytic composition that produces an acetaldehyde mol % that is notably decreased compared to the acetaldehyde mol % obtained using the gamma-alumina without the yttrium oxide.

That is, the results of Comp 1 show a 1.09 mol % of acetaldehyde and the results of Ex 1 show an undetectable level of acetaldehyde, i.e., essentially zero mol %. The results show an increased production of acetone, that is, from 0.16 mol % in Comp 1 to 0.51 mol % in Ex 1. However, addition of the acetaldehyde and acetone concentrations yields a total oxygenate mol % that is decreased by addition of yttrium oxide in the admixture with gamma-alumina, that is, from 1.25 mol % in Comp 1 to 0.51 mol % in Ex 1.

In addition, the production of ethylene shown is slightly decreased by addition of the yttrium oxide from 93.33 mol % in Comp 1 to 91.13 mol % in Ex 1. However, the 2.20 mol % decrease in ethylene production is largely compensated by a 2.07 mol % increase in propylene production, that is, from 0.58 mol % in Comp 1 to 2.65 mol % in Ex 1.

In contrast, forming an admixture of the amorphous aluminosilicate with the yttrium oxide and exposing the ethanol to the catalytic composition produces a mixture of desired products and undesired byproducts in which the mol % of the acetaldehyde is almost unchanged from use of the amorphous aluminosilicate without the yttrium oxide. That is, as shown in the table, Comp 2 has an acetaldehyde mol % of 0.27 and Comp 3 has an acetaldehyde mol % of 0.23. However, the mol % of the acetone is notably increased by exposure to the admixture of the amorphous aluminosilicate with the yttrium oxide as compared to the amorphous aluminosilicate without the yttrium oxide. That is, Comp 2 has an acetone mol % of 0.01 and Comp 3 has an acetone mol % of 0.23.

Hence, addition of the acetaldehyde and acetone concentrations yields a total oxygenate mol % that is increased by addition of yttrium oxide in the admixture with amorphous aluminosilicate, that is, from 0.28 mol % in Comp 2 to 0.69 mol % in Comp 3. The increase in the yield of total oxygenates resulting from addition of yttrium oxide to amorphous aluminosilicate is undesirable because the oxygenate byproducts are reactive molecules that interfere with intended downstream reactions using the olefin product. Accordingly, the in situ decrease in the yield of total oxygenates resulting from addition of yttrium oxide to gamma-alumina is desirable because it reduces a requirement for removing the oxygenate byproducts downstream from the reactor in which the dehydration occurs.

In addition, the production of ethylene is notably decreased from 99.46 mol % in Comp 2 to 89.06 mol % in Comp 3 by addition of the yttrium oxide to the amorphous aluminosilicate. This 10.40 mol % decrease in ethylene production is not compensated for by an increase in propylene production. That is, the 3.15 mol % increase in propylene from 0.05 mol % in Comp 2 to 3.20 mol % in Comp 3 is notably less than the 10.40 mol % decrease in ethylene production shown by comparing Comp 2 to Comp 3.

Addition of the yttrium oxide to the gamma-alumina in Ex 1 and the amorphous aluminosilicate in Comp 3 increased production of $CO_2$ to 3.45-3.61 mol % as an undesired byproduct as compared to 0-0.09 mol % production of $CO_2$ with the gamma-alumina in Comp 1 and the amorphous aluminosilicate in Comp 2. However, removal of $CO_2$ as an undesired byproduct is commonly performed in olefin production and involves less capital input and labor and energy costs than, for example, removal of aldehydes using a distillation column.

Acetaldehyde production can be decreased to levels comparable to that shown in Ex 1 when a particular metal oxide is used with amorphous aluminosilicate, although at temperatures higher than 400° C. Such results (not shown) are obtained when the controlled reaction temperature of the single reaction chamber is held at 425° C. using the amorphous aluminosilicate plus 25% by weight of yttrium oxide under conditions described with regard to Comp 3. Such results (not shown) also are obtained when the controlled reaction temperature of the single reaction chamber is held at 450° C. using a silicoaluminophosphate, which is a zeolite aluminum-containing molecular sieve, plus 25% by weight of yttrium oxide under conditions described with regard to Comp 3. An example of such a silicoaluminophosphate is SAPO-34, synthesis of which is described in U.S. Pat. No. 7,528,201.

Catalytic compounds are chosen based upon a number of productivity factors, which include a preferred conversion percentage and/or rate using a particular substrate, and a preferred selectivity of conversion to a particular product, among other factors. Productivity costs can be reduced by extending a useful life of such catalytic compounds during which a preferred level of the selected productivity factor(s) is maintained. Reducing a temperature at which a catalytic compound is utilized is one way of extending the useful life of the catalytic compound. Hence, costs are reduced by using the admixture of the alumina with the particular metal oxide both by in situ decrease of oxygenate production and by extending the useful life of the catalytic compound by operating at 400° C. rather than higher temperatures.

Additional metal oxides can be used in combination with, or instead of, yttrium oxide. Choice of a particular metal oxide, or combination thereof, depends upon a number of factors, such as the particular alkanol to be dehydrated, changes in the dehydration temperature, pressure, diluent, and/or diluent concentration.

Group numbers and names, e.g., lanthanides and actinides, for the metal elements in the metal oxides described herein are as indicated in the Periodic Table of the Elements shown in the CRC Handbook of Chemistry and Physics 86$^{th}$ Edition 2005-2006 (published in 2005 by CRC Press, Taylor and Francis Group, Boca Raton, Florida). Undesired oxygenate byproduct production is comparably reduced, under conditions similar to those described with regard to Ex 1, when an oxide of a group 3 metal, e.g., yttrium, is used in combination with, or is substituted with, one or more oxides of metals from a number of other groups (results not shown). For example, the alumina dehydration catalyst can form an admixture with one or more oxides of metals from group 1, e.g., lithium, group 3, e.g., yttrium, group 4, e.g., zirconium, group 6, e.g., tungsten, group 7, e.g., manganese, and/or the lanthanides and actinides, e.g., lanthanum.

Accordingly, as described in the present disclosure, a catalytic composition for production of olefins includes an admixture of an alumina and at least one additional metal oxide. The catalytic composition is positioned in a single reaction zone of a fixed bed continuous flow reactor. The metal of the at least one additional metal oxide is an element selected from groups 1, 3, 4, 6, 7 and/or lanthanides and actinides of the Periodic Table of the Elements.

The at least one additional metal oxide is present in an amount within a range of from 5 percent (%) by weight to 50% by weight based upon a total catalytic composition weight. A preferred catalytic composition is an admixture where the alumina dehydration catalyst is gamma-alumina and the metal element in the metal oxide is yttrium.

The present disclosure describes an improved method for producing olefins by alkanol dehydration. The improvement includes using a catalytic composition described herein whereby the production of the olefins has a decreased total oxygenate byproduct. The decreased oxygenate byproduct is relative to the same olefins produced from the same alkanol at the same temperature although using the same alumina dehydration catalyst in an absence of the same at least one additional metal oxide.

The improvement further includes the production of the olefins having a decreased total oxygenate byproduct relative to the same olefins produced from the same alkanol at the same temperature although using a dehydration catalyst consisting of an amorphous aluminosilicate or an aluminum-containing molecular sieve in combination with the same at least one additional metal oxide.

The present disclosure describes increasing production of propylene relative to the propylene produced with the alumina dehydration catalyst in an absence of the at least one additional metal oxide. As an example of an alkanol and an undesired oxygenate byproduct, the present disclosure describes using ethanol as a substrate for the production of the olefins, where a decreased oxygenate byproduct is acetaldehyde.

What is claimed is:

1. An improved method for producing olefins by alkanol dehydration, wherein the improved method comprises decreasing acetaldehyde byproduct by using a catalytic composition consisting of an admixture of an alumina dehydration catalyst and yttrium oxide present in an amount within a range of from 5 percent by weight to 50 percent by weight based upon a total catalytic composition weight, wherein the alkanol is ethanol, whereby the acetaldehyde byproduct is decreased relative to the same olefins produced from the same alkanol at the same temperature although using the same alumina dehydration catalyst in an absence of the yttrium oxide.

2. The improved method of claim 1, further comprising the production of the olefins having a decreased acetaldehyde byproduct relative to the same olefins produced from the same alkanol at the same temperature although using a dehydration catalyst consisting of an amorphous aluminosilicate or an aluminum-containing molecular sieve in combination with the yttrium oxide.

3. The improved method of claim 1, further comprising increasing production of propylene relative to the propylene produced with the alumina dehydration catalyst in an absence of the yttrium oxide.

4. The improved method of claim 1, further comprising positioning the catalytic composition in a single reaction zone of a fixed bed continuous flow reactor.

5. The improved method of claim 1, wherein the catalytic composition comprises gamma-alumina.

6. A method for selective reduction of acetaldehyde byproduct formed during production of an olefin by alkanol dehydration, the method comprising contacting a feed, wherein the feed comprises ethanol, with a catalytic composition consisting of an admixture of an alumina dehydration catalyst and yttrium oxide present in an amount within a range of from 5 percent by weight to 50 percent by weight based upon a total catalytic composition weight to provide an olefin total yield and an acetaldehyde byproduct yield, wherein the acetaldehyde byproduct yield is decreased relative to a corresponding acetaldehyde byproduct yield formed during production of the same olefin produced from the same alkanol at the same temperature although using the same alumina dehydration catalyst in absence of the yttrium oxide.

7. The method of claim 6, wherein the acetaldehyde yield is reduced to essentially zero.

8. The method of claim 6, wherein the catalytic composition comprises gamma-alumina.

* * * * *